United States Patent
Hohlbein

(10) Patent No.: US 7,386,909 B2
(45) Date of Patent: Jun. 17, 2008

(54) TOOTHBRUSH

(75) Inventor: Douglas Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 48 days.

(21) Appl. No.: 10/531,127

(22) PCT Filed: Oct. 24, 2003

(86) PCT No.: PCT/US03/34108

§ 371 (c)(1),
(2), (4) Date: Apr. 8, 2005

(87) PCT Pub. No.: WO2004/039208

PCT Pub. Date: May 13, 2004

(65) Prior Publication Data

US 2005/0278883 A1    Dec. 22, 2005

Related U.S. Application Data

(60) Provisional application No. 60/422,017, filed on Oct. 28, 2002.

(51) Int. Cl.
*A46B 9/04* (2006.01)
*A46B 1/00* (2006.01)

(52) U.S. Cl. .............................. 15/110; 15/167.1; 15/201

(58) Field of Classification Search .................. 15/110, 15/167.1, 188, 201, 187, 186, 191.1
See application file for complete search history.

(56) References Cited

U.S. PATENT DOCUMENTS

| 2,154,846 | A | * | 4/1939 | Heymann et al. | ............ 601/141 |
| 2,206,726 | A |   | 7/1940 | Lasater |   |
| 4,783,869 | A |   | 11/1988 | Lee |   |
| 5,052,071 | A | * | 10/1991 | Halm | .......... 15/167.1 |
| 5,481,775 | A |   | 1/1996 | Gentile et al. |   |
| 5,528,786 | A |   | 6/1996 | Porat et al. |   |
| 5,625,916 | A |   | 5/1997 | McDougall |   |
| 5,651,158 | A | * | 7/1997 | Halm | .......... 15/167.1 |
| 5,735,011 | A |   | 4/1998 | Asher |   |
| 5,802,656 | A |   | 9/1998 | Dawson et al. |   |
| RE35,941 | E |   | 11/1998 | Stansbury, Jr. |   |
| 5,839,149 | A |   | 11/1998 | Scheier et al. |   |
| 6,041,467 | A | * | 3/2000 | Roberts et al. | ............. 15/167.1 |

(Continued)

FOREIGN PATENT DOCUMENTS

| CN | 1261770 | 8/2000 |
| CN | 1346243 | 4/2002 |
| WO | WO9901054 | 1/1999 |
| WO | WO 0047083 | 8/2000 |

*Primary Examiner*—Laura C Guidotti
(74) *Attorney, Agent, or Firm*—Michael J. Wallace, Jr.

(57) ABSTRACT

A toothbrush (10) is disclosed with soft fingers (16) mounted on the toothbrush head (14). During use of the tooth-brush the fingers move laterally relative to the axis of the tooth-brush thereby improving the tooth cleaning and gum massaging performance of the toothbrush. The lateral movement of the fingers is accomplished by relatively stiff ribs (24) which physically interconnect the fingers to flexible portions of the toothbrush head. The ribs translate flexure of the head into the lateral movement of the fingers.

17 Claims, 2 Drawing Sheets

U.S. PATENT DOCUMENTS

| | | |
|---|---|---|
| 6,088,870 A | 7/2000 | Hohlbein |
| 6,141,817 A | 11/2000 | Dawson |
| 6,338,176 B1 | 1/2002 | Smith et al. |
| D466,303 S * | 12/2002 | Saindon et al. .............. D4/104 |
| 6,599,048 B2 | 7/2003 | Kuo |
| 2003/0196283 A1 | 10/2003 | Eliav et al. |

* cited by examiner

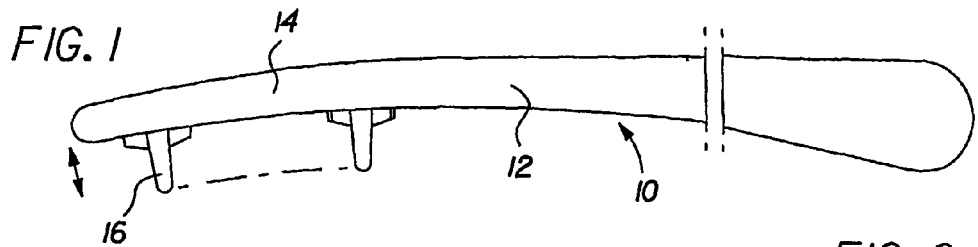
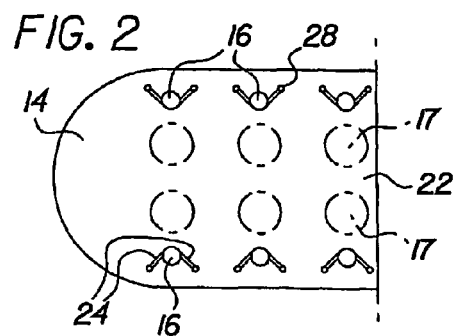
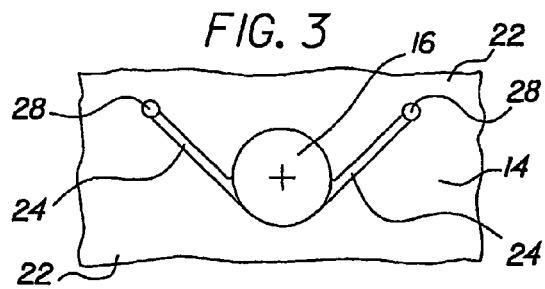
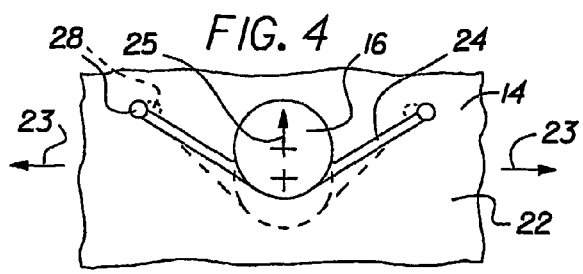
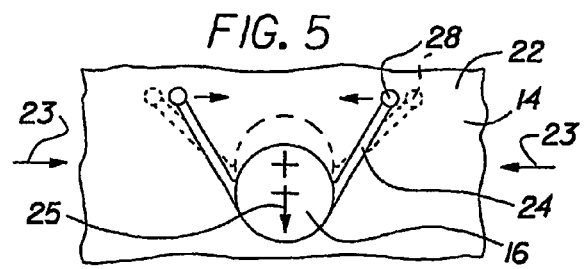
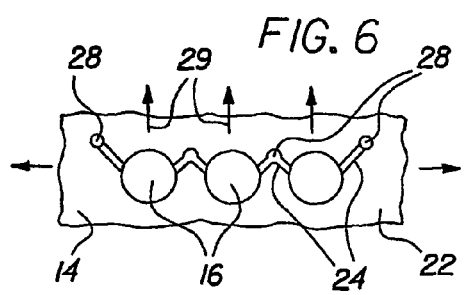
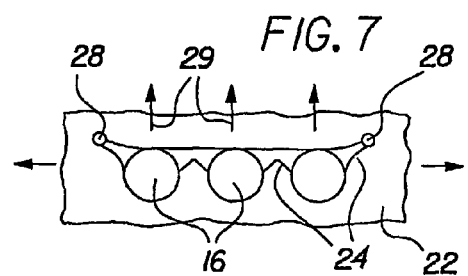
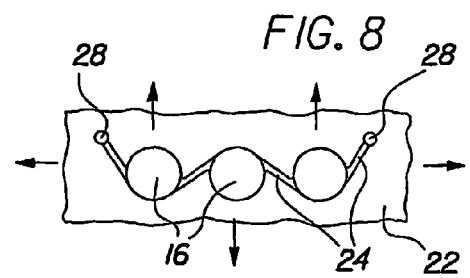
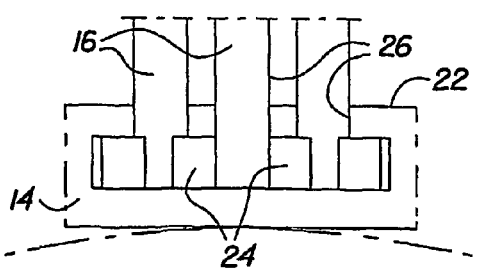

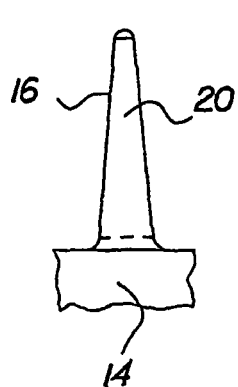
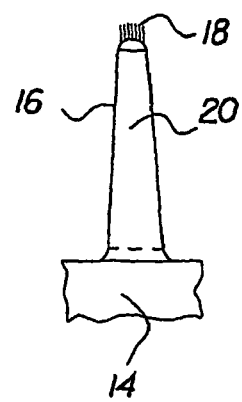
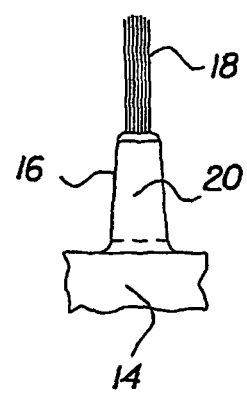
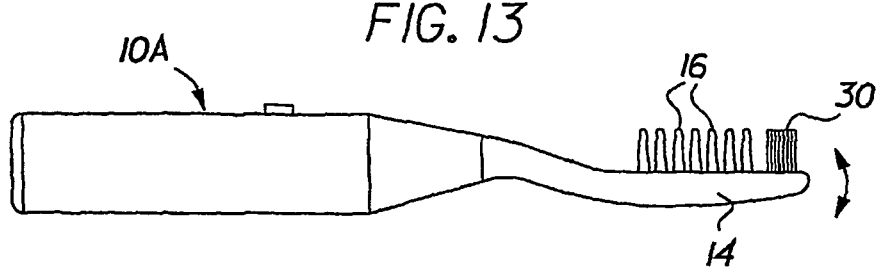
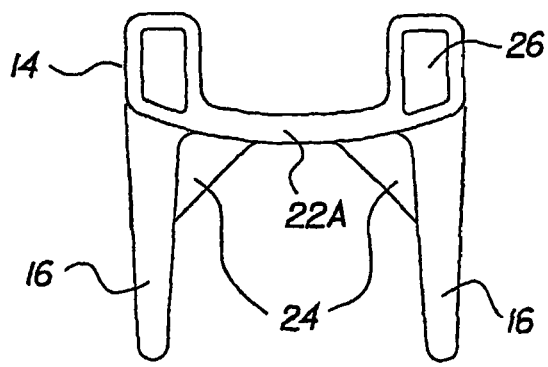
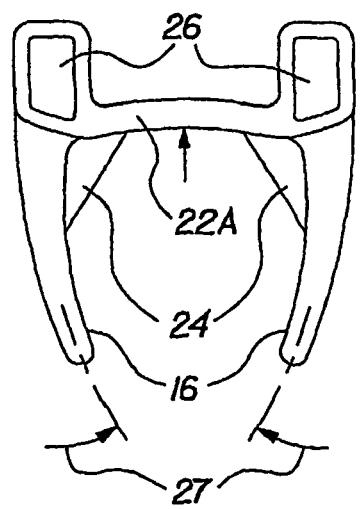

TOOTHBRUSH

This application is a national-stage filing under 35 USC 371 of International Application PCT/US2003/034108, filed on Oct. 24, 2003, which claims priority to U.S. Application 60/422,017 filed Oct. 28, 2002, both of which are incorporated by reference herein in their entirety.

BACKGROUND OF THE INVENTION

The present invention is directed to a toothbrush, either manual or powered, which includes a handle and a head. Cleaning elements are mounted to the head such as tufts of bristles. When toothpaste is applied to the cleaning elements the user inserts the head into the mouth and brushes the teeth in a known manner.

The head of a conventional toothbrush usually has a flat or slightly altered surface to which cleaning elements are attached. Usually the cleaning elements are strands of plastic material(s) formed into tufts, bundles or other groupings. The strands are attached to the head either before or after forming the toothbrush.

The toothbrush of the present invention facilitates more motion of cleaning elements in the toothbrush head thereby promoting healthy stimulation of gums and cleaner teeth. It is well known that the ideal brushing technique from a dental hygiene perspective is an up and down stroke along the vertical surface of teeth which massages the gums while cleaning the teeth. However, due to a number of factors, including ergonomic difficulties, haste, lack of education or the like, few consumers use the recommended brushing technique. Rather, the typical consumer brushes across their teeth in a horizontal motion rather than a vertical movement. Various approaches have been taken by others to translate horizontal brush movement into partial vertical movement of the bristles or cleaning elements.

Translation of horizontal to vertical movement of cleaning elements is accomplished in U.S. Pat. No. 4,783,869 through use of a helix groove in a movable shaft within a toothbrush handle. The groove receives a pin which rides in the groove. This mechanism causes the toothbrush head to partially rotate or oscillate as the handle moves left-to-right or vice versa in the user's mouth. That rotation or oscillation causes the cleaning elements to move in a vertical plane perpendicular to movement of the toothbrush handle.

U.S. Pat. No. 5,481,775 discloses an arcuate shaped base for a toothbrush. head aligned with the longitudinal axis of the head. A movable arcuate block containing cleaning elements is flexibly mounted on the toothbrush head. The block is free to slide on the head in a manner whereby the cleaning elements may travel in a vertical direction generally transverse to the typical side-to-side motion of the toothbrush.

U.S. Pat. No. 5,528,786 discloses pivotal mounting of cleaning elements that allows those elements to move up and down in concert with a side-to-side stroke along the teeth.

A general disclosure of flexible mounting for cleaning elements on a toothbrush head is contained in U.S. Pat. No. 5,839,149. In this patent the cleaning elements are mounted on a flexible membrane supported between a horseshoe shaped handle extension.

U.S. Pat. No. 6,141,817 discloses cleaning elements mounted on a flexible membrane that splay outward when the toothbrush is pressed against the user's teeth.

U.S. Pat. No. 6,338,176 B1 issued Jan. 15, 2002 to Smith, et al. discloses round sections of cleaning bristles mounted on individual pads that rotate within a toothbrush body. This converts backward and forward motion of the toothbrush into circular motion of the cleaning elements (column 1, lines 11-13). The bristles associated with each pad are of varying height to accommodate irregularities, gaps, pockets and contours in natural tooth formation (column 1, lines 40-45). The rotating cleaning elements can be supplemented with fixed cleaning elements adjacent thereto (FIG. 11; column 5, lines 43-49).

SUMMARY OF THE INVENTION

This invention provides transverse movement of cleaning elements relative to the longitudinal axis of a toothbrush head without the cumbersome hinges, mechanisms and helical channels described in the aforementioned prior art toothbrushes. Those prior art toothbrushes using mechanical means to introduce such movement have a common fault of creating interstices and voids in the toothbrush head that can harbor bacteria and germs. The mechanical parts also add to the manufacturing cost of such toothbrushes.

This invention improves the movement of cleaning elements relative to a toothbrush head. That movement is induced by adding appropriately configured fingers to groups of cleaning elements, which fingers are attached by ribs to a flexible head. The ribs are relatively thin, typically rectangular, webs that connect the fingers to a flexible portion of the toothbrush head. As pressure is applied by the user to the toothbrush handle, the flexible portion of the toothbrush head underlying the finger moves. Because the ribs are physically attached to the flexible portion of the head, the movement of the head is translated to the fingers in a manner which causes the fingers to move laterally to the longitudinal axis of the head. This movement of the fingers wipes across teeth thereby providing extra cleaning of the teeth. The movement of the fingers closest to the gumline acts to massage the user's gums.

The "fingers" used in this invention may take a variety of shapes and materials. The entire finger can be made of elastomeric material. Alternatively, only a portion of the finger is made of elastomeric material with the tip facing away from the head comprised of bristles extending from the elastomeric material. Preferably the elastomeric material should extend far enough up the finger height to facilitate attachment of enough rib material to promote movement of the finger in the manner described herein.

BRIEF DESCRIPTION OF THE DRAWINGS

FIG. 1 is a side elevational overview of a toothbrush broken along its length having a flexible head with fingers mounted thereon, showing the ribs interconnecting the finger and flexible head.

FIG. 2 is a fragmental front plan view showing an arrangement of fingers connected by ribs to a flexible head.

FIG. 3 is a fragmental plan view of single finger connected by ribs to an unflexed toothbrush head.

FIGS. 4 and 5 are fragmental plan views of a single finger connected by ribs to a flexible head in flexed positions caused by movement of the flexible head.

FIG. 6-8 are fragmental plan views of multiple fingers interconnected to each other and to a flexible toothbrush head by ribs forming a web between the fingers.

FIG. 9 is a fragmental cross-sectional view in elevation of the fingers mounted in a flexible toothbrush head.

FIGS. 10-12 are fragmental elevational views of the fingers used with the toothbrush of the invention.

FIG. 13 is a side elevational view of a power toothbrush using a flexible head and gum stimulation fingers.

FIGS. 14 and 15 are cross sectional views of the fingers with ribs interconnecting the fingers to a flexible portion of the toothbrush head.

DETAILED DESCRIPTION OF INVENTION

FIGS. 1 and 2 illustrate a toothbrush 10 with a handle 12 and head 14. Mounted on or in head 14 are fingers 16, preferably having a tapered shape. As shown in FIG. 2 fingers 16 are preferably arranged about the periphery of head 14. That location materially assists the gum massaging effect of the finger movement contemplated by this invention. More particularly, when the longitudinal axis of toothbrush 10 is perpendicular to the axis of teeth being brushed, as is typical with most users, the fingers 16 are closest to the gumline.

The fingers 16 are preferably flexible and soft to the touch. Accordingly they may be formed of a soft elastomeric material. The general shape of fingers 16 is illustrated in FIGS. 10-12. As so illustrated they are tapered and comprise all elastomeric material (FIG. 10) or a set of bristles 18 partially surrounded by elastomeric material 20 (FIGS. 11 and 12). The elastomeric material should extend along the length of finger 16 a sufficient distance to facilitate attachment of ribs as described in more detail below.

To facilitate the therapeutic movement of fingers 16 it is important that head 14 of toothbrush 10 be flexible and that. fingers 16 be flexibly mounted in head 14. FIG. 9 illustrates one form of flexible mounting of fingers in head 14. In this embodiment the head 14 has a box-like shape in cross section. At least the upper face 22 of head 14, and preferably the entirety of head 14, is made of a flexible material so that the axes of fingers 16 can move relative to the plane of toothbrush 10. The fingers 16 project from apertures 26 in the flexible upper face 22 of head 14. Any rib and finger 16 arrangement shown in FIGS. 6-8 can be molded into the toothbrush head 14. This flexible mounting in a flexible portion 22 of head 14 assists in obtaining the desired lateral movement of fingers relative to the axes of toothbrush 10. The role of ribs in obtaining that movement is explained below.

Another means of imparting movement to the fingers 16 is illustrated in FIGS. 14 and 15. As illustrated, fingers 16 are physically linked to a flexible face 22A of head 14 by angled rib 24. Rib 24 can be integrally molded into head 14 and finger 16 during the manufacture of toothbrush 10. It can also be formed of a more rigid (than elastomeric) material such as polypropylene in order to enhance lateral movement of fingers 16. Flexible face 22A of head 14 in this embodiment can be molded around frame members 26 forming the outer periphery of head 14. These frame members 26 of head 14 may be attached to handle 12 of toothbrush 10 in a known manner.

The role of ribs 24 and flexible head 14 in imparting lateral movement to fingers 16 is illustrated in FIGS. 2-5. FIG. 2 illustrates the location of fingers 16 and ribs along outer edges of flexible face 22 of head 14. Other groups of bristles or cleaning elements 17 are arranged inboard of fingers 16 as illustrated in FIG. 2. Fingers 16 on the outer edge of head 14 are closest to the gum line when the user holds the toothbrush in a normal position, i.e., with the longitudinal axis perpendicular to the axis of the user's teeth. Ribs 24 extend from the side of finger 16 to the face 22 or 22A of flexible head 14. These ribs can have a triangular, trapezoidal or like shape that interconnect the finger 16 to the face of flexible head 14. This interconnection assures lateral movement of finger 16 as the face 22 or 22A deflects outward or inward along the longitudinal axis when in use as described below.

The lateral movement of finger 16 is illustrated in the sequence shown in FIGS. 3-5. In FIG. 3 there is no deflection of face 22 or 22A of flexible head 14. FIG. 4 represents a deflection of face 22 that stretches that face as shown by the arrows 23 at the edge of this fragmental view. When so stretched the ends 28 of rib 24 anchored to face 22 move away from each other. That movement exerts a lateral force on finger 16 causing it to move laterally toward the outside periphery of head 14 as indicated by the arrow 25 in FIG. 4. Conversely, when deflection of face 22 or 22A of head 14 causes that face to compress, the ribs 24 push finger 16 laterally in the opposite direction as indicated by the arrow 25 in FIG. 5. Thus, as various forces are transmitted to flexible face 22 or 22A of head 14 during use, that head moves in compression or expansion. That movement causes fingers 16 to move in a lateral direction thereby promoting tooth cleaning and gum stimulation.

Another embodiment of the invention illustrated in FIGS. 14 and 15 shows ribs 24 oriented approximately 90 degrees to the longitudinal axis of toothbrush 10 versus approximately 45 degrees shown in FIGS. 2-5. In the former embodiment, movement of the flexible face 22A in an upward direction (FIG. 15) causes lateral inward movement of fingers 16 as illustrated by the arrows 27 in this Figure. Conversely, downward movement of flexible face 22A would cause lateral movement of fingers 16 away from each other toward the outside of head 14 (not illustrated).

Other arrangements of ribs 24 and their attachment to fingers 16 are illustrated in FIGS. 6-8. As illustrated, multiple fingers 16 are interconnected by a continuous rib 24. FIG. 6 illustrates the interconnecting ribs 24 on one side of fingers 16. Thus, upon deflection of flexible face 22 or 22A of head 14 all fingers 16 move in the same direction as indicated by the arrows 29 in FIGS. 6 and 7. If it were desirable to have the fingers 16 move in different directions the arrangement of ribs 24 shown in FIG. 8 can be utilized.

Any suitable form of cleaning elements may be used as the cleaning elements 17 in the broad practice of this invention. The term "cleaning elements" is intended to be used in a generic sense which could include conventional fiber bristles or massage elements or other forms of cleaning elements such as elastomeric fingers or walls arranged in a circular cross-sectional shape or any type of desired shape including straight portions or sinusoidal portions.

It is to be understood that the specific illustration of the cleaning elements is merely for exemplary purposes. The invention can be practiced with various combinations of the same or different cleaning element configurations (such as stapled or in-molded technology bristles, etc.) and/or with the same bristle or cleaning element materials (such as nylon bristles, spiral bristles, rubber bristles, etc.). Similarly, while FIG. 2 illustrates the cleaning elements to be generally perpendicular to head 14, some or all of the cleaning elements may be angled at various angles with respect to the outer surface of head 14. It is thereby possible to select the combination of cleaning element configurations, materials and orientations to achieve specific intended results to deliver additional oral health benefits, like enhanced cleaning, tooth polishing, tooth whitening and/or massaging of the gums.

FIG. 13 illustrates a powered toothbrush 10A containing the fingers 16 of the invention mounted on a flexible head 14 of the toothbrush. Cleaning elements 17 are preferably mounted inboard of fingers 16 as illustrated in FIG. 2. This embodiment includes a power driven movable disc or section 30 having cleaning elements. The movable section 30 could be oscillated rotationally such as by using the type of drive mechanism shown in U.S. Pat. No. 5,625,916, or could move in and out using the type of drive mechanism shown in U.S. Patent No. 35,941; all of the details of both patents are incorporated herein by reference thereto. Although FIG. 13 shows movable section 30 to be at the distal end of the head, the movable section(s) could be located at any desired location on the head.

The invention claimed is:

1. A toothbrush comprising a handle having a longitudinal axis, a flexible head secured to the handle, the head being flexibly mounted to the handle along the longitudinal axis, the head having an upper face with fingers flexibly mounted thereon, and ribs connecting the fingers to the upper face, whereby flexure of the head under compression or expansion along the longitudinal axis causes a longitudinal movement of ends of the ribs with respect to each other and a lateral movement of the fingers relative to the longitudinal axis.

2. The toothbrush of claim 1 wherein at least a portion of fingers comprise a soft elastomeric material.

3. The toothbrush of claim 2, wherein a composition of the rib material is stiffer than the elastomeric material of the fingers.

4. The toothbrush of claim 1 wherein the fingers are mounted in openings in the upper face of the head.

5. The toothbrush of claim 1 wherein the ribs interconnecting the fingers and flexible face are formed from polypropylene.

6. The toothbrush of claim 1 wherein the fingers include adjacent fingers that are connected by off-center ribs on one side of the adjacent fingers whereby all fingers connected by the ribs move in the same lateral direction when the head is flexed along the longitudinal axis.

7. The toothbrush of claim 1 wherein the fingers include adjacent fingers that are connected by off-center ribs on opposite sides of the adjacent fingers whereby the adjacent fingers move in opposite lateral directions when the head is flexed along the longitudinal axis.

8. The toothbrush of claim 1 wherein the head contains fingers along at least one edge of the head and cleaning elements are at least another portion of the head.

9. The toothbrush of claim 8 wherein the cleaning elements are moved by a powered source in the toothbrush.

10. A toothbrush comprising a handle having a longitudinal axis, a flexible head secured to the handle, the head being flexibly mounted to the handle along the longitudinal axis, the head having an upper face with a finger flexibly mounted thereon, and ribs extending from the upper face and connecting the finger to the upper face, the ribs being disposed at an acute angle to the longitudinal axis, whereby flexure of the head under compression or expansion along the longitudinal axis causes a lateral movement of the finger relative to the longitudinal axis.

11. The toothbrush of claim 10 wherein at least a portion of the finger comprises an elastomeric material.

12. The toothbrush of claim 11, wherein the ribs are stiffer than the elastomeric material of the finger.

13. The toothbrush of claim 10 wherein the finger extends through an aperture in the face of the head.

14. The toothbrush of claim 10 wherein the finger comprises multiple fingers being connected by ribs on one side of the fingers whereby all fingers connected by the ribs move in one lateral direction when the head is flexed along the longitudinal axis.

15. The toothbrush of claim 10 wherein the finger comprises multiple fingers being connected by ribs on opposite sides of the fingers whereby the fingers move in opposite lateral directions when the head is flexed along the longitudinal axis.

16. The toothbrush of claim 10 wherein the finger comprises multiple fingers connected by ribs and some of the fingers are disposed along at least one edge of the head, and the head comprises cleaning elements disposed thereon.

17. The toothbrush of claim 16 wherein the cleaning elements are moved by a powered source in the toothbrush.

* * * * *